United States Patent
Duan et al.

(10) Patent No.: US 11,525,118 B2
(45) Date of Patent: Dec. 13, 2022

(54) **BACILLUS HAVING EFFECT OF INDUCING CORN TO RESIST NORTHERN CORN LEAF BLIGHT (*EXSEROHILUM TURCICUM*) OF CORN AND APPLICATION**

(71) Applicant: Shenyang Agricultural University, Shenyang (CN)

(72) Inventors: Yuxi Duan, Shenyang (CN); Ning Liu, Shenyang (CN); Lijie Chen, Shenyang (CN); Xiaofeng Zhu, Shenyang (CN); Haiyan Fan, Shenyang (CN); Yuanyuan Wang, Shenyang (CN); Xiaoyu Liu, Shenyang (CN); Jichen Yan, Shenyang (CN)

(73) Assignee: Shenyang Agricultural University, Liaoning (CN)

( * ) Notice: Subject to any disclaimer, the term of this patent is extended or adjusted under 35 U.S.C. 154(b) by 384 days.

(21) Appl. No.: 16/839,726

(22) Filed: Apr. 3, 2020

(65) Prior Publication Data
US 2020/0362425 A1   Nov. 19, 2020

(30) Foreign Application Priority Data
May 13, 2019   (CN) .......................... 201910391696.8

(51) Int. Cl.
| | |
|---|---|
| *A01N 63/20* | (2020.01) |
| *A01C 1/06* | (2006.01) |
| *A01C 1/08* | (2006.01) |
| *C12N 1/20* | (2006.01) |
| *C05G 3/60* | (2020.01) |
| *C12R 1/11* | (2006.01) |

(52) U.S. Cl.
CPC ................ *C12N 1/205* (2021.05); *A01C 1/06* (2013.01); *A01C 1/08* (2013.01); *A01N 63/20* (2020.01); *C12N 1/20* (2013.01); *C05G 3/60* (2020.02); *C12R 2001/11* (2021.05)

(58) Field of Classification Search
None
See application file for complete search history.

(56) References Cited

U.S. PATENT DOCUMENTS

2020/0362425 A1* 11/2020 Duan ....................... C12N 1/20

* cited by examiner

*Primary Examiner* — Alton N Pryor
(74) *Attorney, Agent, or Firm* — Lee & Hayes, P.C.

(57) ABSTRACT

The disclosure relates to *bacillus* having an effect of inducing corn to resist Northern leaf blight and applications of the *bacillus*. The *bacillus* having an effect of inducing corn to resist Northern corn leaf blight is *Bacillus megaterium* which was deposited on Apr. 16, 2019 with a deposit number of CGMCC No. 17573. The *Bacillus megaterium* of the disclosure can induce corn to generate resistance to Northern corn leaf blight during seed germination and corn growth to activate the immune response of corns and stimulate immune control of Northern leaf blight of corn. The method described herein is long in coming does not pollute environment and soil, is a green, simplified and new control method of Northern leaf blight of corn, and has wide application and popularization prospect.

13 Claims, No Drawings

BACILLUS HAVING EFFECT OF INDUCING CORN TO RESIST NORTHERN CORN LEAF BLIGHT (*EXSEROHILUM TURCICUM*) OF CORN AND APPLICATION

CROSS REFERENCE TO RELATED APPLICATION

This application claims the benefit of Chinese Patent Application No. 201910391696.8, filed on May 13, 2019, which is hereby incorporated by reference in its entirety.

TECHNICAL FIELD

The disclosure belongs to the technical field of microbial pesticides, and particularly relates to *bacillus* having the effect to induce the resistance of corn to the Northern corn leaf blight (*Exserohilum turcicum*).

BACKGROUND

Northern leaf blight of corn (*Exserohilum turcicum*) is one of the most important leaf diseases generally occurring in corn production, which was first reported in Italy in 1876, and then spread all over America, Europe, Asia, Africa and other corn producing areas. The occurrence of Northern leaf blight of corn was first recorded in 1899 in China, and then spread all over the country, especially in the cold and cool corn producing areas from the northeast, north, northwest and south mountainous areas. (Dong Jingao. Agricultural plant pathology (the Third Edition) [M]. Beijing: China Agricultural Press, 2001.) Northern leaf blight of corn can cause a large area of corn leaves to die, resulting in the loss of corn yield. In recent years, due to the single variety of corn and the lack of varieties resisting Northern leaf blight, the occurrence of Northern leaf blight of corn has increased with global warming and the change of cultivation modes. At present, the main methods for preventing and controlling Northern leaf blight of corn are to plant disease-resistant varieties and via control through the use of chemical agents. However, the Northern leaf blight disease mainly becomes serious in the middle and later stage of plant growth. This is because the plants are tall so that it is difficult to spray chemical agents, the chemical pesticides seriously pollute the environment, and many chemical pesticides have been banned in succession. Therefore, research on biological control has naturally become a hot issue. Exploring the biological control method with the characteristics of high control effect, no toxicity and no pollution is a new way to prevent and control this disease.

Currently, biological control bacterium resources for control of Northern leaf blight of corn include fungi, bacteria and actinomycetes. The current research mainly involves screening biocontrol bacteria by antagonizing with the pathogen of Northern leaf blight of corn or to obtain biocontrol bacteria by spraying potted leaves. An Application method for controlling the Northern leaf blight of corn is leaf spraying or smearing. Since Northern leaf blight is a disease occurring during the adult-plant stage of corn, pesticide applying is difficult, and it is difficult for such a method to be practically applied in production.

The technical problem to be solved by the disclosure is that the disclosure provides a *bacillus* which can stimulate the immune system of corn through seed coating, and can achieve the effect of stimulating the host to resist Northern leaf blight through seed coating treatment. A simple and practical new method for stimulating the immune control of a disease of corn at the adult-plant stage through seed coating treatment can activate the defense response of plants. At present, there are no research reports on the control of Northern leaf blight of corn by the above methods in the world.

SUMMARY

In order to overcome the defects of the control technology of Northern leaf blight of corn in the current technologies, the disclosure provides *bacillus* having an effect of inducing corn to resist Northern leaf blight. The *bacillus* can induce corn to produce resistance to Northern leaf blight during the seed germination and plant growth through seed coating treatment before sowing. Such treatment may, for example, activate the defense response of corn, stimulate immune control of Northern leaf blight of corn. Moreover, the treatment, does not pollute the soil and environment, simplifies control methods of Northern leaf blight of corn, and has good development and application prospect.

The objective of the disclosure is achieved by the following technical solution: provided herein is *bacillus* having an effect of inducing corn to resist Northern corn leaf blight and methods of using the *bacillus*, wherein the *bacillus* having an effect of inducing corn to resist Northern corn leaf blight is *Bacillus megaterium*. The *Bacillus megaterium* is classified as *Bacillus megaterium* Sneb85. It was deposited on Apr. 16, 2019, with the deposit number CGMCC No. 17573, at the General Microbiology Center of China Microbial Species Conservation Management Committee, which has an address of Institute of Microbiology, Chinese Academy of Sciences, No. 3, No. 1 courtyard, Beichen West Road, Chaoyang District, Beijing. The deposit is available to the public upon grant of a patent disclosing this strain.

An application method of *bacillus* having an effect of inducing corn to resist Northern leaf blight of may include the following steps:

(1) Activation and Culture of Strains

Single strain is obtained by plate culture of *Bacillus megaterium* using solid bacterium medium.

The formula of the bacterial culture medium is as follows: beef extract peptone agar culture medium (NA): beef extract 3-5 grams (g), peptone 10 g, sucrose 10 g, agar 17-20 g, distilled water 1000 mL, and pH 7.0.

(2) Liquid Fermentation Culture

The strains obtained after activation culture are inoculated into a liquid medium, the fermentation temperature is 25-28° C., the rotating speed of a shaking table is 150 rpm' and the fermentation time is 2-3 days.

The formula of the liquid fermentation medium is as follows: beef extract 3 g, peptone 10 g, sucrose 10 g, distilled water 1000 mL, and pH 7.0.

(3) Coating Treatment

The concentration of the fermentation broth of *Bacillus megaterium* obtained in step (2) reaches $1 \times 10^7$ CFU·ml$^{-1}$ or more; the fermentation broth is treated with seed coating or seed dressing in a mass ratio of liquid to seeds of 1:40 (namely, 40 g of seeds corresponds to 1 g of fermentation broth).

The disclosure has the following beneficial effects:

(1) Through the field screening and indoor and outdoor tests of fermentation broth of 8755 strains of microorganisms' fermentation broth, the disclosure explores a new method for controlling Northern leaf blight of corn by seed immune stimulation. The Sneb85 fermentation broth of *Bacillus megaterium* has corn inducing activity, and can be used for seed treatment of corn, has the effect of resisting Northern leaf blight of corn, thereby solving the problem of controlling Northern leaf blight of corn with biological bacteria.

(2) A method according to the present disclosure adopts seed coating treatment of *Bacillus megaterium* fermentation broth to stimulate immune control of Northern leaf blight of corn; this method is a simple and efficient new method for controlling Northern leaf blight of corn, and can activate the defense response of corn.

(3) The corn seed treatment as described herein has a long control time for Northern leaf blight and does not cause pollution to the environment and soil, and is a green and light disease control method.

DESCRIPTION OF THE EMBODIMENTS

In order to further describe but not limit the disclosure in detail, the following examples are given. The terms "a," "an," "the" and similar referents used in the context of describing the claimed subject matter (especially in the context of the following claims) are to be construed to cover both the singular and the plural, unless otherwise indicated herein or clearly contradicted by context.

As will be understood by one of ordinary skill in the art, each embodiment disclosed herein can comprise, consist essentially of, or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. In particular embodiments, lack of a material effect is evidenced by lack of a statistically-significant reduction in the embodiment's ability to induce resistance of corn to Northern leaf blight.

When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±15% of the stated value; ±10% of the stated value; ±5% of the stated value; ±4% of the stated value; ±3% of the stated value; ±2% of the stated value; ±1% of the stated value; or ±any percentage between 1% and 20% of the stated value.

The disclosure describes fermentation broth comprising isolated *Bacillus megaterium* and liquid fermentation culture medium, wherein the *Bacillus (B.) megaterium* is deposited with the General Microbiology Center of China Microbial Species Conservation Management Committee (CGMCC), Beijing, China, on Apr. 16, 2019, and accorded Deposit No. 173573, and wherein the fermentation broth induces resistance of corn to Northern leaf blight. In embodiments, the fermentation broth also includes beef extract, peptone, sucrose, and/or water. The concentration of *B. megaterium* in the fermentation broth includes at least $1\times10^7$ CFU/ml. In embodiments, the concentration of *B. megaterium* in the fermentation broth is about $1\times10^7$ CFU/ml, about $1\times10^8$ CFU/ml, about $1\times10^9$ CFU/ml, or about $1\times10^{10}$ CFU/ml. In embodiments, the disclosure describes a composition including the fermentation broth.

The disclosure also describes a method of preparing the fermentation broth described herein, wherein the method includes culturing a single strain of *B. megaterium* to obtain an activated *B. megaterium*, inoculating a liquid fermentation culture medium with the activated *B. megaterium*, and growing the activated *B. megaterium* in the liquid fermentation culture medium to a concentration of at least about $1\times10^7$ CFU/ml thereby obtaining the fermentation broth. In embodiments, the liquid fermentation culture medium includes beef extract, peptone, sucrose, and/or water. In embodiments, culturing the single strain of *B. megaterium* to obtain activated *B. megaterium* includes growing *B. megaterium* on a solid bacterium medium. In embodiments, the method described herein includes growing the activated *B. megaterium* at a temperature of 25 to 28° C. for about two or three days in the liquid fermentation culture medium using a rotary shaker at a speed of 150 rpm (revolutions per minute). In embodiments, the method includes growing the activated *B. megaterium* to a concentration of about $1\times10^7$ CFU/ml, about $1\times10^8$ CFU/ml, about $1\times10^9$ CFU/ml, or about $1\times10^{10}$ CFU/ml.

The disclosure also describes a method of using the fermentation broth described herein or a composition comprising the fermentation broth described herein to induce resistance of corn to Northern leaf blight. The method of inducing resistance of corn to Northern leaf blight includes treating corn seeds with the fermentation broth and sowing the treated corn seeds or planting the treated corn seeds in the ground. In embodiment, treating the corn seeds includes coating the corn seeds with the fermentation broth with kneading followed by drying the coated seed in the shade. In embodiments, coating the corn seeds is carried out at a mass ratio of 40 grams of corn seeds to 1 gram of fermentation broth.

EXAMPLES

Example 1

Preparation of *Bacillus* Fermentation Broth Having an Effect of Inducing Corn to Resist Northern Leaf Blight.

The *bacillus* having an effect of inducing corn to resist Northern leaf blight is *Bacillus megaterium*. The *Bacillus megaterium* is classified as *Bacillus megaterium* Sneb85 and was deposited on Apr. 16, 2019 with deposit number CGMCC No. 17573, at the General Microbiology Center of China Microbial Species Conservation Management Committee, and conservation address is Institute of Microbiology, Chinese Academy of Sciences, No. 3, No. 1 courtyard, Beichen West Road, Chaoyang District, Beijing.

The method of culturing and activating the *bacillus* having an effect of inducing corn to resist Northern leaf blight of corn may include the following steps:

(1) Activation and Culture of Strains

Single strain was obtained by plate culture of *Bacillus megaterium* for 3 days (d) at 28° C. using a solid bacterium medium.

The formula of the bacterial culture medium was as follows: beef extract peptone agar culture medium (NA): beef extract 3 g, peptone 10 g, sucrose 10 g, agar 17-20 g, distilled water 1000 mL, and pH 7.0.

(2) Liquid Fermentation Culture

The strains obtained after activation culture were inoculated into a liquid fermentation medium, the fermentation temperature was 25-28° C., the rotating speed of a shaking table was 150 r·min$^{-1}$ and the fermentation time was 2-3 d.

The formula of the liquid fermentation medium was as follows: beef extract 3 g, peptone 10 g, sucrose 10 g, distilled water 1000 mL, and pH 7.0.

The concentration of the fermentation broth of the obtained *Bacillus megaterium* reached $1\times10^7$ CFU·ml$^{-1}$ or more.

Example 2

Field Effect Test for Controlling Northern Leaf Blight of Corn with *Bacillus megaterium* Sneb85 Fermentation Broth Test site: Corn experimental field, Kangping County, Shenyang City, Liaoning Province. The Northern leaf blight of corn was serious in this experimental field last year;

Corn variety: Zhengdan958, and seeds were purchased on the market.

Treatment:

Treatment 1 was seed coating treatment with *Bacillus megaterium* Sneb85 fermentation broth;

Treatment 2 was uncoated (CK1) corn seeds;

Treatment 3 was coating with beef extract peptone liquid culture medium (CK2);

Coating treatment method: corn seeds were coated with the prepared *Bacillus megaterium* fermentation broth having adjusted concentration in example 1; the surfaces of corn seeds were first disinfected with 5.0% sodium hypochlorite solution for 5 min, then washed with sterile water for 3-5 times, and dried. Coating treatment was carried out in a mass ratio of liquid to seeds of 1:40 (namely, 40 g of seeds corresponds to 1 g of fermentation broth). In order to make the coating uniform, the seeds were kneaded in the coating process, then dried in the shade, and then seeded.

Field Control Effect:

At the mature stage of corn plants, the disease progression of Northern leaf blight of corn was investigated and the control effect was calculated. The results showed that the disease index of Northern leaf blight of corn treated with an Sneb85 fermentation product was less than that for the control, and the field control effect was 58.94% in Kangping City, Shenyang City, Liaoning Province. There was significant difference between the coated corn and the untreated corn. It can be seen that corns coated with Sneb85 fermentation broth before sowing can produce resistance to Northern leaf blight of corn at the maturity stage, and the disease resistance effect of corns is induced to be relatively stable, showing a good control effect.

TABLE 1 field control effect of corn seeds coated with Sneb85 fermentation broth product

| Treatment | Disease index | Control effect |
|---|---|---|
| Sneb85 | 35.6 | 58.94% |
| CK1 (uncoated) | 93.3 | — |
| CK2 (beef extract peptone liquid culture medium) | 86.7 | — |

All publications, patents and patent applications cited in this specification are incorporated herein by reference in their entireties as if each individual publication, patent or patent application were specifically and individually indicated to be incorporated by reference.

The subject matter described above is provided by way of illustration only and should not be construed as limiting. Various modifications and changes may be made to the subject matter described herein without following the example embodiments and applications illustrated and described, and without departing from the true spirit and scope of the present disclosure, which is set forth in the following claims.

What is claimed is:

1. A fermentation broth comprising *Bacillus megaterium* and liquid fermentation culture medium, wherein the *Bacillus (B.) megaterium* is deposited with the General Microbiology Center of China Microbial Species Conservation Management Committee (CGMCC), Beijing, China, and accorded Deposit No. 17573, and wherein the fermentation broth induces resistance of corn to Northern leaf blight.

2. The fermentation broth of claim 1, wherein the fermentation broth further comprises beef extract, peptone, sucrose, and/or water.

3. The fermentation broth of claim 1, wherein the fermentation broth comprises *B. megaterium* at a concentration of at least about $1\times10^7$ CFU/ml.

4. The fermentation broth of claim 3, wherein the fermentation broth comprises *B. megaterium* at a concentration of about $1\times10^7$ CFU/ml, about $1\times10^8$ CFU/ml, about $1\times10^9$ CFU/ml, or about $1\times10^{10}$ CFU/ml.

5. A method of preparing the fermentation broth of claim 1, wherein the method comprises culturing a single strain of *B. megaterium* to obtain an activated *B. megaterium*, inoculating a liquid fermentation culture medium with the activated *B. megaterium*, and growing the activated *B. megaterium* in the liquid fermentation culture medium to a concentration of at least about $1\times10^7$ CFU/ml thereby obtaining the fermentation broth of claim 1.

6. The method of claim 5, wherein culturing the single strain of *B. megaterium* to obtain activated *B. megaterium* comprises growing *B. megaterium* on a solid bacterium medium.

7. The method of claim 5, wherein the liquid fermentation culture medium comprises beef extract, peptone, sucrose, and/or water.

8. The method of claim 7, wherein growing the activated *B. megaterium* comprises growing at a temperature of about 25 to 28° C. for about two or three days in the liquid fermentation culture medium.

9. The method of claim 8, wherein growing the activated *B. megaterium* comprises shaking the in the liquid fermentation culture medium with a rotating speed of 150 rpm.

10. The method of claim 5, wherein the method comprises growing the activated *B. megaterium* to a concentration of about $1\times10^7$ CFU/ml, about $1\times10^8$ CFU/ml, about $1\times10^9$ CFU/ml, or about $1\times10^{10}$ CFU/ml.

11. A method of inducing resistance of corn to Northern leaf blight comprising treating corn seeds with the fermentation broth of claim 1 and planting the treated corn seeds.

12. The method of claim 11, wherein treating the corn seeds comprises coating the corn seeds with the fermentation broth with kneading and drying the coated seed in the shade prior to planting.

13. The method of claim 12, wherein the coating is carried out at a mass ratio of 40 grams of the corn seeds to 1 gram of the fermentation broth.

* * * * *